United States Patent [19]

Chiang

[11] 4,433,061

[45] Feb. 21, 1984

[54] RADIOIMMUNOASSAY FOR CYCLIC NUCLEOTIDES

[75] Inventor: Chih-Sheng Chiang, Chatsworth, Calif.

[73] Assignee: American Hospital Supply Corporation, Evanston, Ill.

[21] Appl. No.: 269,155

[22] Filed: Jun. 1, 1981

[51] Int. Cl.³ ................. G01N 33/56; G01N 33/58; G01N 33/60
[52] U.S. Cl. ................................... 436/542; 436/539; 436/804; 436/815; 436/828; 435/7
[58] Field of Search ................ 424/1, 12; 23/230 B; 435/7; 436/539, 542, 804, 815, 828

[56] References Cited

U.S. PATENT DOCUMENTS 3,937,698 2/1976 Gutcho et al. ............... 424/180 X
4,038,033 7/1977 Monks et al. ................. 424/1 X
4,115,538 9/1978 Satoh et al. .................. 424/1

OTHER PUBLICATIONS

Goldberg, Clin. Chem., 23:576–580 (1977).
Tsang et al., J. Clin. Endocrinol. Met., 35:809–817 (1972).

*Primary Examiner*—Christine M. Nucker
*Attorney, Agent, or Firm*—Roger A. Williams

[57] ABSTRACT

An improved radioimmunoassay for the determination of cyclic nucleotides in body fluids which comprises adding a source of divalent cation prior to assay minimizes the effects of both endogenous calcium ion and EDTA used as an anticoagulant in blood plasma samples.

16 Claims, No Drawings

RADIOIMMUNOASSAY FOR CYCLIC NUCLEOTIDES

This invention relates to an improved process for the determination of cyclic nucleotides in a nucleotide containing body fluid. It has been discovered, however, that endogenous calcium ion interferes with the radioimmunoassay (RIA) of cyclic nucleotides.

The need for more rapid and accurate analytical methods for determining the concentration of cyclic nucleotides has increased markedly due to the numerous microanalytical studies in biochemical research and due to routine clinical testing for physicians and hospitals. The determination of adenosine 3',5'-cyclic monophosphate (cAMP), for example, can be quite useful in the diagnosis of various disease states such as hyperparathyroidism, a condition characterized by elevated plasma calcium concentration. Few methods are presently available to meet this ever-growing demand.

Radioimmunoassay (RIA) would appear to be ideally suited for clinical laboratory use. The highly sensitive RIA does not require time consuming and arduous sample prepurification. The procedure is simple to perform by laboratory technicians utilizing only a very small sample of body fluid. [Goldberg, M. L., Clin. Chem., 23, 576 (1976), Harper, J. F. and Brooker, G., J. Cyc. Nucltd. Res., 1, 207 (1975).]

However, it has been discovered that both endogenous calcium ion as well as ethylenediaminatetracetic acid (EDTA), which is used as an anticoagulant in blood plasma samples collected for cyclic nucleotide assay, cause significant decreases in the cyclic nucleotide values obtained by RIA. The interference of cyclic nucleotide analysis by RIA due to endogenous calcium ion is particularly disconcerting in the diagnosis of hyperparathyroidism. Although readily diagnosed by cAMP determination of blood plasma, conventional methods of RIA yield results greatly in error due to the abnormal endogenous calcium ion concentration in the plasma of patients suffering from this disease state.

The interference in cyclic nucleotide determination by RIA resulting from the use of EDTA as an anticoagulant in the collection of blood plasma may be avoided by the use of other anticoagulants such as heparin. Previous studies have established, however, that the treatment of blood plasma with EDTA prevents degradation of cyclic nucleotides. Accordingly, the use of EDTA as an anticoagulant in blood plasma samples destined for cyclic nucleotide determination is preferred. [Murad, F., Adv. Cyclic Nucleotide Res., 3, 355 (1973); Broadus, A. E., et al., Ann. N.Y. Acad. Sci., 185, 50 (1971); Tsang, P. W., Lehotay, D. C., and Murphy, B. E., J. Clin. Endocrinol. Metab., 35, 809 (1972).]

The interference in the determination of cyclic nucleotides by RIA caused by endogenous calcium ion and EDTA can be minimized by the addition of a divalent cation source such as calcium ion or magnesium ion to the sample of body fluid to be analyzed. The addition of a divalent cation such as calcium ion, in addition to minimizing the interference of endogenous calcium ion and EDTA in the determination of cyclic nucleotides by RIA, increases the antibody's affinity for analyte (cyclic nucleotide) increasing the sensitivity of the RIA and allowing for the use of less antibody per test.

As used herein, the term "a source of divalent cation" is taken to mean any substantially soluble salt of calcium or magnesium. The preferred divalent cation for use in this invention is calcium ion. Suitable calcium salts are calcium acetate, calcium formate, calcium nitrate, calcium sulfate, calcium iodide, calcium bromide and calcium chloride. Calcium chloride is the preferred source of calcium ion.

As used herein the term "cyclic nucleotide" includes adenosine 3',5'-cyclic monophosphate (cAMP), guanosine 3',5'-cyclic monophosphate (cGMP), cytidine 3',5'-cyclic monophosphate (cCMP), uridine 3',5'-cyclic monophosphate (cUMP), and thymine 3',5'-cyclic monophosphate (cTMP).

As used herein the term "body fluid" includes blood plasma, urine and cerebrospinal fluid (CSF) as well as tissue homogenates.

The effect of the addition of calcium ion on adenosine 3',5'-cyclic monophosphate (cAMP) binding to its corresponding antibody is shown in Table 1.

TABLE 1

| $Ca^{2+}$ Addition mM | cAMP Binding to Antibody % Maximum Binding |
|---|---|
| 0.0 | 48.0 |
| 0.2 | 73.5 |
| 0.6 | 77.4 |
| 2.0 | 83.6 |
| 6.0 | 93.5 |
| 10.0 | 99.9 |
| 20.0 | 100.0 |
| 40.0 | 99.8 |
| 50.0 | 99.7 |
| 100.0 | 96.0 |

It can be seen that cAMP binding to antibody increases with increasing calcium ion concentration up to approximately 10 mM at which concentration the binding reaches a plateau. By adding approximately 10–20 mM calcium ion, the interference resulting from small amounts of endogenous calcium ion (normally 13–26 nanomoles/liter of plasma) and the use of EDTA will be "bufferred". That is, the resulting effective calcium ion concentration will be within the limits of optimal cAMP binding to antibody. The addition of 15 mM calcium ion is preferred.

The amount of divalent cation needed to minimize the interference of endogenous calcium ion and EDTA for the other cyclic nucleotides can be determined in a similar manner employing standard art recognized procedures.

Table 2 illustrates the effect of EDTA and endogenous calcium ion on the RIA of cAMP where no divalent cation is added to minimize the resulting interference.

TABLE 2

| Additions to Sample (Final Concentration) | cAMP(nmoles/liter) Value | Change in cAMP Value (%) |
|---|---|---|
| no additions | 10.0 | — |
| 0.02 mM EDTA | 16.4 | +64 |
| 0.02 mM $CaCl_2$ | 7.1 | −29 |

Table 3 illustrates the effect of EDTA and endogenous calcium on the RIA of cAMP where the samples are treated with calcium chloride (sufficient to raise the calcium ion concentrations 15 mM) in order to minimize the effects of these agents.

TABLE 3

| Additions to Sample (Final Concentration) | cAMP(nmoles/liter) Value | Change in cAMP Value (%) |
|---|---|---|
| no additions | 20.3 | — |

TABLE 3-continued

| Additions to Sample (Final Concentration) | cAMP(nmoles/liter) Value | Change in cAMP Value (%) |
|---|---|---|
| 0.06 mM EDTA | 20.0 | −1.5 |
| 0.06 mM CaCl$_2$ | 19.3 | +4.9 |

Clearly the RIA methods of the prior art, illustrated by Table 2, result in cAMP values greatly in error. However, the present RIA method, illustrated by Table 3, results in cAMP values which are only slightly effected by additions of EDTA and endogenous calcium ion.

The following example illustrates the best mode presently employed for practicing the process of this invention:

EXAMPLE 1

Adenosine 3',5'-cyclic monophosphate (cAMP) in acidified EDTA containing plasma, is acetylated by adding acetic anhydride in triethylamine. Anti-cAMP (the antibody corresponding to cAMP obtained from Collaborative Research as a gelatin containing solution) binds acetylated cAMP and $^{125}$I-2'-O-succinyl-cAMP-tyrosine methyl ester (also obtained from Collaborative Research) more avidly than nonacetylated cAMP. Acetylated cAMP in a sample competes with $^{125}$I-2'-O-succinyl-cAMP-tyrosine methyl ester (tracer) for binding to anti-cAMP. Calcium chloride in acetate buffer (sufficient to raise the calcium concentration 15 mM), $^{125}$I-2'-O-succinyl-cAMP-tyrosine methyl ester and anti-cAMP are added to the acetylated sampleS. After equilibration, an aqueous 2% S. aureous cell suspension (protein A source, obtained as a lyophilized powder from Enzyme Center) is added. Antibody bound tracer is bound by the S. aureous cells and can be quantitated by determining the amount of radioactivity in the S. aureous cell pellet. A standard displacement curve (using known amounts of cAMP) is constructed and used to determine the cAMP values in unknowns.

Although the invention has been illustrated by the preceding example of a cAMP determination, it is not to be construed as being limited to the particular embodiments or materials disclosed therein. Rather, the invention encompasses the generic area hereinbefore disclosed, that is the radioimmunoassay of cyclic nucleotides in body fluids wherein the interference of endogenous calcium ion as well as EDTA is minimized by the addition of a source of divalent cation. Various modifications and embodiments thereof can be made without departing from the spirit and scope thereof.

I claim:

1. In a process for the determination of a cyclic nucleotide in a cyclic nucleotide containing body fluid by radioimmunoassay comprising the steps of admixing the body fluid, an antibody for the cyclic nucleotide, and a tracer; permitting reaction to occur for binding the tracer; separating bound tracer from free tracer; and measuring either the bound or free tracer to quantitatively determine the cyclic nucleotide, the improvement comprising the step of adding a source of divalent cation in an amount sufficient to minimize the interference of endogenous calcium ion while admixing the antibody, tracer and body fluid.

2. The process of claim 1 wherein said divalent cation source is a calcium ion source.

3. The process of claim 2 wherein said calcium ion source is calcium chloride.

4. The process of claim 2 wherein said cyclic nucleotide is adenosine 3',5'-cyclic monophosphate.

5. The process of claim 2 wherein said cyclic nucleotide is guanosine 3',5'-cyclic monophosphate.

6. The process of claim 2 wherein the amount of calcium ion added to the sample is in the range of 10–20 mM.

7. The process of claim 2 wherein said body fluid is blood plasma.

8. The process of claim 1 wherein said divalent cation source is magnesium ion source.

9. The process of claim 8 wherein said magnesium ion source is magnesium chloride.

10. The process of claim 8 wherein the amount of magnesium ion added to the sample is in the range of 10 to 20 mM.

11. In a process for the determination of a cyclic nucleotide in a body fluid containing such cyclic nucleotide by radioimmunoassay comprising the steps of admixing the body fluid, ethylenediaminatetracetic acid, an antibody for the cyclic nucleotide, and a tracer; permitting reaction to occur for binding the tracer; separating bound tracer from free tracer; and measuring either the bound or free tracer to quantitatively determine the cyclic nucleotide, the improvement comprising the step of adding a source of divalent cation in an amount sufficient to minimize the interference of endogenous calcium ion while admixing the antibody, ethylenediaminatetracetic acid, tracer and body fluid.

12. The process of claim 11 wherein said divalent cation source is a calcium ion source.

13. The process of claim 11 wherein said divalent cation source is a magnesium ion source.

14. The process of claim 11 wherein said cyclic nucleotide is adenosine 3',5'-cyclic monophosphate.

15. The process of claim 11 wherein said cyclic nucleotide is guanosine 3',5'-cyclic monophosphate.

16. In a process for the determination of a cyclic nucleotide in a body fluid containing such cyclic nucleotide by radioimmunoassay comprising the steps of admixing the body fluid, ethylenediaminatetracetic acid, an antibody for the cyclic nucleotide, and a tracer; permitting reaction to occur for binding the tracer; separating bound tracer from free tracer; and measuring either the bound or free tracer to quantitatively determine the cyclic nucleotide, the improvement comprising the step of adding a source of calcium ion in an amount sufficient to minimize the interference of endogenous calcium ion while mixing the body fluid, ethylenediaminetetracetic acid, antibody and tracer.

* * * * *